(12) United States Patent
Nakayama et al.

(10) Patent No.: US 6,432,632 B2
(45) Date of Patent: *Aug. 13, 2002

(54) FLUORESCENCE POLARIZATION METHOD

(75) Inventors: Hiroshi Nakayama, Hirakata; Jinsei Miyazaki, Higashiosaka, both of (JP)

(73) Assignee: Matsushita Electric Industrial Co., Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,603
(22) PCT Filed: Sep. 4, 1998
(86) PCT No.: PCT/JP98/03988
§ 371 (c)(1),
(2), (4) Date: Jul. 23, 1999
(87) PCT Pub. No.: WO99/13332
PCT Pub. Date: Mar. 18, 1999

(30) Foreign Application Priority Data

Sep. 5, 1997 (JP) .............................. 9-240672

(51) Int. Cl.[7] .............................. C12Q 1/70; C12Q 1/68; G01N 33/53; A61K 39/395
(52) U.S. Cl. .............................. 435/5; 435/6; 435/7.1; 435/7.2; 424/130.1; 424/147.1; 424/152.1
(58) Field of Search .............................. 435/5, 7.1, 6, 7.2, 435/7.32, 7.37, 7.9, 7.91, 968; 536/164, 172; 424/130, 147.1, 148.1, 149.1, 150.1, 158.1, 159.1

(56) References Cited

U.S. PATENT DOCUMENTS

| | | | |
|---|---|---|---|
| 4,629,783 A | * 12/1986 | Cosand | 530/324 |
| 5,094,819 A | * 3/1992 | Yager et al. | 422/82.07 |
| 5,230,998 A | * 7/1993 | Neurath et al. | 435/7.1 |
| 5,607,847 A | * 3/1997 | Harris et al. | 435/69.6 |
| 5,660,991 A | * 8/1997 | Lakowicz et al. | 435/7.1 |
| 5,869,237 A | * 2/1999 | Ward et al. | 435/6 |

FOREIGN PATENT DOCUMENTS

| | | |
|---|---|---|
| EP | 088 974 A2 | 9/1983 |
| WO | WO 97/39326 | 10/1997 |

OTHER PUBLICATIONS

Rose et al.; Manual of Clinical Laboratory Immunology 5th Ed.; AMS Press; pp. 407, 408, 449, 607, 846–849, and 960, Apr. 1997.*
Dandliker, W.B. and de Saussure, V.A., "Fluorescence polarization in immunochemistry" *Immunochemistry* 7:799–828 (1970).
European Search Report for Application No. 98941732.4.
Rhys Williams, A.T. and Smith, D.S., "Fluorescence Polarization Immunoassay" *Methods of Immunological Analysis* Rene F. Masseyeff ed. VCH, Weinheim, Germany pp.466–475 (1993).
Spencer, R.D., et al., "Design, Construction, and Two Applications for an Automated Flow–Cell Polarization Fluorometer with Digital Read Out: Enzyme–Inhibitor (Antitrypsin) Assay and Antigen–Antibody (Insulin–Insulin Antiserum) Assay" *Clin. Chem.* 19(8):838–844 (1973).
Urios, P. and Cittanova, N., "Adaptation of Fluorescence Polarization Immunoassay to the Assay of Macromolecules" *Analytical Biochemistry* 185:308–312 (1990).

* cited by examiner

*Primary Examiner*—Hankyel T. Park
*Assistant Examiner*—Stacy S. Brown
(74) *Attorney, Agent, or Firm*—Jacqueline F. Mahoney; Judy M. Mohr; Perkins Coie LLP (57) ABSTRACT

A fluorescence polarization method for analyzing an assay-object in a sample is provided. The fluorescence polarization method includes the steps of: (a) providing a fluorescent-labeled protein in which a protein is covalently bound to a fluorochrome(s), wherein the protein is capable of specifically binding to the assay-object; (b) allowing the fluorescent-labeled protein to bind to the assay-object; and (c) measuring a change in the degree of fluorescence polarization which has taken place in the fluorescent-labeled protein by its binding to the assay-object.

18 Claims, 8 Drawing Sheets

FIG.1

FIG. 2 A diagram showing synthesis scheme of succinimidyl-1-pyrenebutanoic acid

FLUORESCENCE POLARIZATION METHOD

This application claims priority to application no. PCT/JP98/03988, filed Sep. 4, 1998, which claims the priority of Japanese application no. 9-240672, filed Sep. 5, 1997, which are both incorporated herein by reference.

TECHNICAL FIELD

The present invention relates to a fluorescence polarization method for analyzing an assay-object in a sample. In particular, the present invention relates to a fluorescence polarization method useful in analyzing a bacteria or a virus in a sample. The present invention is useful in the fields of art of medical diagnosis, environmental assay, and food control relevant to food poisoning and infectious diseases.

BACKGROUND ART

The fluorescence polarization method is known in the art as a method for assaying a substance in a sample. The method is based on the principle that when a fluorescent-labeled compound is excited by linearly polarized light, the fluorescence emitted from the compound has a degree of polarization which is in proportion to the molecular weight thereof.

As a fluorescence polarization method which has been developed, there is a fluorescence polarization immunossay based on an antigen-antibody reaction.

Figure 8:
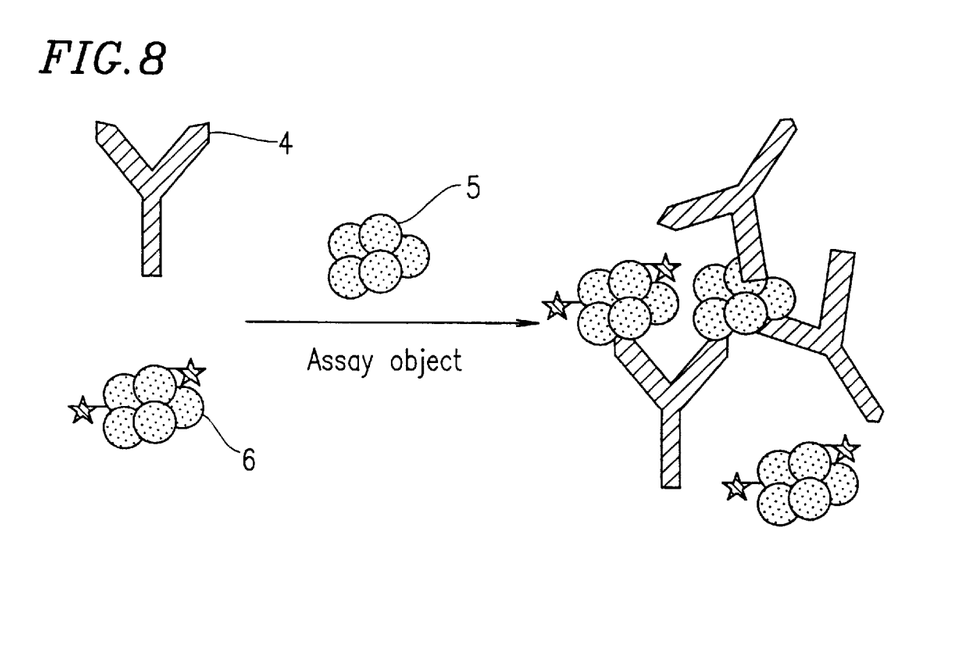
FIG. 8 is a concept diagram showing the assay principle of a conventional fluorescence polarization method.

For example, U.S. Pat. No. 4,902,630 discloses an assay method (FIG. 8 is a concept diagram showing the assay principle) in which a body fluid (particularly, a blood) containing CRP (5), an assay-object, is added to a mixed solution which contains: a "tracer" (6) obtained by binding fluorescein, a fluorochrome, to C-reactive protein (CRP); and an antibody (4) which specifically binds to CRP. CRP (5) in the sample is assayed based on competition between the tracer (6) and CRP (5) for the antibody (4) in the mixed solution. Since this assay system is based on a competitive reaction, it requires a two-step binding reaction, thereby complicating the assay operation. Moreover, fluorescein used in the assay has a short lifetime of the fluorescence, and thus it is difficult to apply it in an assay for a high-molecular-weight substance.

Japanese Patent Application No. 62-38363 discloses an immunoassay apparatus for an assay of an antigen or antibody utilizing an immunoreaction. It is taught that a fluorescent-labeled antibody can be used in the assay. However, the application describes no specific embodiment of the assay. As an assay-object, it only accounts for a substance, such as a therapeutic drug existing in the blood (e.g., digoxin), whose molecular weight is clearly lower than that of a coexisting protein.

Thus, there has been a demand for development of a fluorescence polarization method with a simple assay reaction system and an easy assay operation, and particularly a method which is suitable for an assay of a high-molecular-weight substance.

DISCLOSURE OF THE INVENTION

An object of the present invention is to provide a fluorescence polarization method for analyzing an assay-object contained in a sample by measuring a change in the degree of the fluorescence polarization thereof, particularly a method which is suitable for an assaying of a high-molecular-weight substance. Another object of the present invention is to provide a reagent for analyzing an assay-object contained in a sample utilizing a fluorescence polarization method.

The present invention relates to a fluorescence polarization method for analyzing an assay-object in a sample, the method including the steps of: (a) providing a fluorescent-labeled protein in which a protein is covalently bound to a fluorochrome(s), wherein the protein is an antibody, a receptor or an inhibitor, which is capable of specifically binding to the assay-object; (b) allowing the fluorescent-labeled protein to bind to the assay-object; and (c) measuring a change in the degree of fluorescence polarization which has taken place in the fluorescent-labeled protein by its binding to the assay-object.

In the above-described method, the antibody capable of specifically binding to the assay-object may be a polyclonal antibody, a monoclonal antibody, a chimeric antibody, a Fab antibody or a (Fab)2 antibody.

In the above-described method, the assay-object may be a biological substance; a microorganism including a bacteria; a virus; a drug; an environmental pollutant or an abused drug. The biological substance may be a peptide, a protein, a lipid, a saccharide or a nucleic acid. The protein as a biological substance may have a molecular weight of 500,000 or more.

The protein as a biological substance may be an antibody, a hormone, an inflammation marker, a coagulation factor, an apolipoprotein, a high density lipoprotein (HDL), a low density lipoprotein (LDL), a glycosylated albumin, a glycosylated hemoglobin, a hemoglobin, a cancer marker or an enzyme.

The hormone may be chorionic gonadotropin, thyroid-stimulating hormone, progesterone, follicular forming hormone, parathyroid-stimulating hormone, adrenocorticotropic hormone, or insulin.

The inflammation marker may be C-reactive protein (CRP), α1-antitrypsin (α1-AT), α1-antichymotrypsin (α1-X), α1-acid glycoprotein (α1-AG), haptoglobin (Hp), ceruloplasmin (Cp), the 9th component of complement (C9), the 4th component of complement (C4), the 3rd component of complement (C3), complement factor B (B), fibrinogen (Fbg), serum amyloid A (SAA), C1 inhibitor (C1I), a sialoglycoprotein (i.e., a glycoprotein to which a sialic acid is bound), an acid-soluble protein (ASP) or an immunosuppressive acidic protein (IAP).

The present invention also relates to a reagent for use in a fluorescence polarization method for analyzing an assay-object in a sample, the reagent including a fluorescent-labeled protein in which a protein is covalently bound to a fluorochrome, wherein the protein is an antibody, a receptor or an inhibitor, which is capable of specifically binding to the assay-object.

The present invention further relates to a fluorescence polarization method for analyzing a bacteria or a virus in a sample, the method including the steps of: (a) providing a fluorescent-labeled antibody in which an antibody is covalently bound to a fluorochrome, wherein the antibody is capable of specifically binding to the bacteria or the virus; (b) allowing the fluorescent-labeled antibody to bind to the bacteria or the virus; and (c) measuring a change in the degree of fluorescence polarization which has taken place in the fluorescent-labeled antibody by its binding to the bacteria or the virus.

In the above-described method, the antibody may be a polyclonal antibody, a monoclonal antibody, a chimeric antibody, a Fab antibody or a (Fab)2 antibody.

In the above-described method, the bacteria may be selected from the group consisting of Rhodospirillaceae, Chromatiaceae, Chlorobiaceae, Myxococcaceae, Archangiaceae, Cystobacteraceae, Polyangiaceae, Cytophagaceae, Beggiatoaceae, Simonsiellaceae, Leucotrichaceae, Achromatiaceae, Pelonemataceae, Spirochaetaceae, Spirillaceae, Pseudomonadaceae, Azotobacteraceae, Rhizobiaceae, Methylomonadaceae, Halobacteriaceae, Enterobacteriaceae, Vibrionaceae, Bacteroidaceae, Neisseriaceae, Veillonellaceae, Organisms oxidizing ammonia or nitrite, Organisms metabolizing sulfer and sulfer compounds, Organisms depositing iron and/or manganese oxides, Siderocapsaceae, Methanobacteriaceae, Aerobic and/or facultatively anaerobic Micrococcaceae, Streptococcaceae, Anaerobic Peptococcaceae, Bacillaceae, Lactobacillaceae, Coryneform group of bacteria, Propionibacteriaceae, Actinomycetaceae, Mycobacteriaceae, Frankiaceae, Actinoplanaceae, Dermatophilaceae, Nocardiaceae, Streptomycetaceae, Micromonosporaceae, Rickettsiaceae, Bartonellaceae, Anaplasmataceae, Chlamydiaceae, Mycoplasmataceae and Acholeplasmataceae.

In the above-described method, the virus may be selected from the group consisting of Enterovirus, Cardiovirus, Rhinovirus, Aphthovirus, Calicivirus, Orbivirus, Reovirus, Rotavirus, Abibirnavirus, Piscibirnavirus, Entomobirnavirus, Alphavirus, Rubivirus, Pestivirus, Flavivirus, Influenzavirus, Pneumovirus, Paramyxovirus, Morbillivirus, Vesiculovirus, Lyssavirus, Coronavirus, Bunyavirus, Arenavirus, Human immunodeficiency virus, Hepatitis A virus, Hepatitis B virus and Hepatitis C virus.

In the fluorescence polarization method of the present invention, fluorochrome may have a functional group which can bind to a primary, secondary or tertiary amino group, a carboxyl group, a thiol group, a phenyl group, a phenol group or a hydroxyl group. The lifetime of the fluorescence of the fluorochrome may be in the range of 10 nanoseconds to 200 nanoseconds. The fluorochrome may have a skeletal structure of rhodamine, pyrene, dialkylaminonaphthalene or cyanin.

The present invention also relates to a reagent for use in a fluorescence polarization method for analyzing a bacteria or a virus in a sample, the reagent including a fluorescent-labeled antibody in which an antibody is covalently bound to a fluorochrome, wherein the antibody is capable of specifically binding to the assay-object.

BEST MODE FOR CARRYING OUT THE INVENTION

Figure 1:
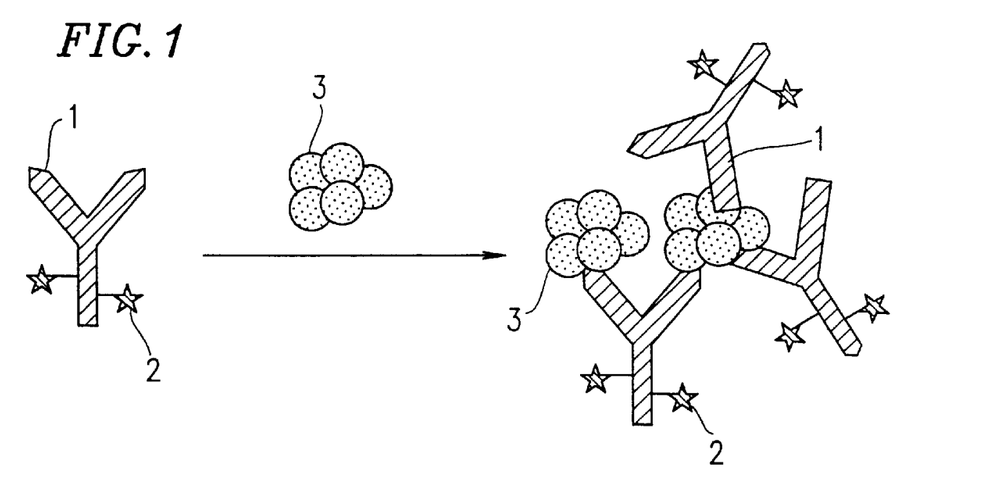
FIG. 1 is a concept diagram showing the principle of the present invention in the case where a fluorescent-labeled antibody is used.

In an assay system of the method of the present invention, a protein is labeled with a fluorescent substance, wherein the protein is an antibody, a receptor or an inhibitor, which is capable of specifically binding to the assay-object. By mixing the fluorescent-labeled protein with the assay-object, the presence of the assay-object can be confirmed. FIG. 1 shows the principle of the present invention in the case where a fluorescent-labeled antibody is used. By mixing a fluorescent-labeled antibody, which is obtained by labeling an antibody (1) which is capable of specifically binding to the assay-object with a fluorochrome (2), with the assay-object (3), the presence of the assay-object (3) is confirmed. Since the reaction required for the assay is a single-step reaction, the reaction system can be simplified, thereby simplifying the assay operation as well as shortening the assay time.

In the assay system of the present invention, a change in molecular weight concomitant with the binding of the fluorescent-labeled protein to the assay-object is measured as a change over time in the molecular orientation. Thus, by selecting the fluorochrome in consideration of the change in the molecular weight before and after the binding, it is possible to assay various assay-objects of high molecular weight (about 500,000 or more), e.g., an assay-object having a size which is equal to or greater than a virus (about 20 nanometers (nm) or more as a particle). The same type of fluorochrome can be used for various assay-objects with different molecular weights so long as the fluorochrome has a lifetime of fluorescence corresponding to the change in the molecular weight before and after the binding.

The present invention will be described below in further detail.

With the fluorescence polarization method of the present invention, it is possible to analyze (i.e., quantify, detect or identify) an assay-object in a sample based on the above-described principle of the fluorescence polarization method.

By covalently binding the protein, which is classified either as an antibody, a receptor or an inhibitor, and which is capable of specifically binding to the assay-object (hereinafter, referred to as the "specifically-binding protein"), with a fluorochrome, a fluorescent-labeled protein useful in the method of the present invention is provided.

The specifically-binding protein has a desired binding property with respect to the assay-object. The specifically-binding protein is a protein, which is classified as any of antibodies, receptors or inhibitors, so long as it has a functional group which allows for the binding to the fluorochrome. An antibody is particularly preferred for its broad spectrum of applications. The antibody type includes a polyclonal antibody, a monoclonal antibody, a chimeric antibody, a Fab antibody and a (Fab)2 antibody. Any type of antibody can be applied to the method of the present invention. A receptor can be used in the case where the assay-object acts as a ligand for the receptor. For example, an inhibitor can be used in the case where the assay-object is an enzyme.

For the fluorochrome, those having a functional group which can be covalently bound to a functional group of the specifically-binding protein (typically, a primary, secondary or tertiary amino group, a carboxyl group, a thiol group, a phenyl group, a phenol group or a hydroxyl group) are utilized. Especially, in the case where a protein such as an antibody is used as the specifically-binding protein, in terms of the binding efficiency, a fluorochrome having an activated functional group (e. g., a halogenated sulphonyl group, a succinimidized carboxyl group, or an isothiocyanated primary amino group) is desired.

The number of fluorochrome molecules bound to one molecule of the labeled object (i.e., the specifically-binding protein) can be varied arbitrarily. It is preferred in order to increase the detection sensitivity to bind 2 or more fluorochromes. However, when more fluorochromes than necessary are bound, it may adversely affect a property of the specifically-binding protein. For example, it may reduce the affinity, solubility, or the like, of the antibody. Therefore, the above-described binding number is preferably 10 or less and, more preferably, one.

When selecting the skeletal structure of the fluorochrome to be used, the excitation wavelength, the fluorescence wavelength, the Stokes shift and the lifetime of the fluorescence are important. Preferably, either or both of the excitation wavelength and/or the fluorescence wavelength exist in the visible light wavelength range (i. e., 300 nm to 700 nm). Preferably, the difference in wavelength between the excitation wavelength and the fluorescence wavelength (i.e., the Stokes shift) is at least 20 nm or more. The lifetime of the fluorescence (the fluorescence relaxation time) of the fluorochrome is typically selected from the range of about 10 nanoseconds to about 1,000 nanoseconds and, preferably, selected from the range of about 10 nanoseconds to about 200 nanoseconds. A fluorochrome having an excessively long fluorescence lifetime which exceeds about 1,000 nanoseconds is not preferred since the degree of polarization can hardly be maintained because of the long lifetime no matter how big the assay-object is. In selecting the lifetime of the fluorescence, the change in molecular weight of the fluorescent-labeled protein through the binding to the assay-object is taken into consideration. This is because the degree of polarization of fluorescence emitted from the fluorescent-labeled protein bound to the assay-object is in a proportional relationship with the size of the molecule.

Specifically, when the change in the molecular weight is about 5,000 to about 50,000 (i.e., when the molecular weight of the assay-object is several thousands to several ten thousands), a fluorochrome having a lifetime of the fluorescence of about 1 to about 15 nanoseconds is preferred. Examples of such a fluorochrome include cyanin and rhodamine. When the change in the molecular weight is about 50,000 to about 500,000 (i.e., when the molecular weight of the assay-object is about several ten thousands to several hundred thousands), a fluorochrome having a lifetime of the fluorescence of about 10 nanoseconds to about 150 nanoseconds is preferred. Examples of such a fluorochrome include dialkylaminonaphthalenes and pyrene derivatives. When the change in the molecular weight is about 500,000 to about 5,000,000 (i.e., when the molecular weight of the assay-object is about several hundred thousands to several millions), a fluorochrome having a lifetime of the fluorescence of about 100 nanoseconds to about 1,000 nanoseconds is preferred. Examples of such a fluorochrome include pyrene derivatives and metal complexes.

From the above-described points of view, preferred examples of fluorochrome include fluorochromes having a skeletal structure of rhodamine, pyrene, a dialkylaminonaphthalene, cyanin, or the like. A particularly preferred fluorochrome may be a fluorochrome having a skeletal structure of a dialkylaminonaphthalene or pyrene.

The reaction for forming the covalent bond between the specifically-binding protein and the fluorochrome can be carried out according to conditions well known to those skilled in the art. When the specifically-binding protein has a primary, secondary or tertiary amino group, a carboxyl group, a thiol group, a phenyl group, a phenol group or a hydroxyl group, the covalent bond can be formed by reacting the specifically-binding protein and the fluorochrome having an activated functional group normally at room temperature for several hours. After the completion of the reaction, the unreacted fluorochrome can be easily removed by an ordinary method (e.g., gel filtration or dialysis). The specifically-binding protein and the fluorochrome can be bound directly or can be bound indirectly via a bifunctional linker molecule, or the like.

Using the above-described fluorescent-labeled protein, it is possible to analyze the assay-object in a sample as follows.

The sample containing the assay-object and the fluorescent-labeled protein are mixed with each other in a solution so as to measure the degree of fluorescence polarization of the fluorescent-labeled protein in the mixed solution. If necessary, the degree of fluorescence polarization of the fluorescent-labeled protein in the absence of the assay-object is also measured. Any polarization measurement apparatus can be used for measuring the degree of fluorescence polarization. The measurement is performed at a mild temperature (about 10 degree centigrade (° C.) to about 40° C.) and, preferably, at a constant temperature.

The measurement of the degree of fluorescence polarization can be performed by measuring the degree after a predetermined time from the mixing of the assay-object and the fluorescent-labeled protein, or by measuring a change in the degree of fluorescence polarization for a unit of time. By taking a measurement at the time when the binding between the assay-object and the fluorescent-labeled protein has been completely finished, more reproducible measurement values are obtained. By measuring the change in the degree of fluorescence polarization for a unit of time while the binding reaction between the assay-object and the fluorescent-labeled protein is in progress, on the other hand, a quicker measurement is possible. For the purpose of identifying the assay-object, a measurement value of a degree of fluorescence polarization for a known standard sample is compared with the measurement value for the unknown assay-object in the sample. For the purpose of quantifying the assay-object contained in the sample, a standard curve is provided through a measurement of the degree of fluorescence polarization using a solution containing a known concentration of the assay-object so as to compare it with the measurement value for the sample.

With the fluorescence polarization method of the present invention, it is possible to perform a quick measurement for a protein having a high molecular weight, particularly about 1,000,000 or more, and a bacteria or a virus, which has been difficult in the past. Therefore, the method of the present invention is preferred in assaying an object, particularly, those having a high molecular weight. The fluorescence polarization method of the present invention is particularly useful in that it is possible to identify the type of bacteria or virus.

The sample intended to be used with the method of the present invention is a material including an assay-object desired to be analyzed in any fields of art including medical diagnosis, environmental assay, and food control. Exemplary samples for medical diagnosis include body fluids including a blood, a lymph, and a tissue fluid. Exemplary samples for environmental assay include materials collected from soil, a river, the air, or the like. Exemplary samples for food control include an extract from ground meat, and an extract from a chopping board. The sample can be in any form so long as it can be used with the method of the present invention.

The assay-objects of the method of the present invention include, though are not limited to, a biological substance, a microorganism, a virus, a pharmaceutical, an environmental pollutant and an abused drug. Preferably, the assay-object is a high molecular weight substance having a molecular weight of about 20,000 to 30,000 or more, more preferably, about 100,000 to 200,000 or more, even more preferably, about 500,000 or more and, most preferably, about a million or more. Alternatively, the assay-object is preferably a substance having a size of about 2 nm or more, more preferably, about 10 nm or more and, most preferably, about 20 nm or more.

The biological substance refers to any organic or inorganic substance existing in the body of a human or other mammal. Typical examples of the biological substance include a peptide, a protein, a lipid, a saccharide and a nucleic acid. Herein, the peptide as a biological substance refers to those having a molecular weight of less than about 1,000. The protein as a biological substance refers those having a molecular weight of about 1,000 or more. Examples of the protein include an antibody, a hormone, an inflammation marker, a coagulation factor, an apolipoprotein, a high density lipoprotein (HDL), a low density lipoprotein (LDL), a glycosylated albumin, a glycosylated hemoglobin, a hemoglobin, a cancer marker and an enzyme. Examples of the cancer marker include, though not limited to, α-fetoprotein (AFP), CEA, CA19-9, ferritin, an immunosuppressive acidic protein (IAP), $\beta_2$-microglobulin (BMG), TPA, polyamine, a polyamine fraction, basic fetoprotein (BFP), SCC antigen, neural specific enolase (NSE), sialyl Le-i antigen (SLX), CYFRA21-1, CA15-3, BGA225, estrogen receptor (ER), progesterone receptor (PgR), 5'-nucleotide phosphodiesterase isozyme-V (5'-NPD-V), vitamin K deficiency protein II (PIVKA-II), CA19-9, elastase I, CA50, SPan-1, DUPAN-2, KMO I, NCC-ST-439, CA125, CA130, CA72-4, sialyl Tn antigen (STN), $SP_4$, fee-HOG-β, PAP, PA, γ-seminoprotein (γ-Sm), and the like.

The microorganism includes a bacteria, a fungus and a protozoan. As the assay-object, a bacteria may be important, Enterobacteriaceae and Vibrionaceae may be more important, and salmonella and enterohemorrhagic *Escherichia coli* belonging to Enterobacteriaceae and Vibrio parahaemolyticus belonging to Vibrionaceae may be particularly important. The virus includes a bacterial virus, a plant virus and an animal virus. As the assay-object, Human immunodeficiency virus (AIDS virus), Hepatitis A virus, Hepatitis B virus and Hepatitis C virus may be particularly important. The pharmaceutical includes any agent used for treating or diagnosing a human or other mammals. The environmental pollutant includes any substance causing environmental pollution which can be detected from soil, a river, the air, or the like. The abused drug refers to a drug, intake of which by a human is restricted by law or regulation, and which has been used in violation of the restriction.

The present invention also provides a reagent including a fluorescent-labeled protein which is suitable for use in the above-described method. The fluorescent-labeled protein may be provided in various forms such as a dry form, a solution form wherein the protein is dissolved in a buffer solution, or the like.

The following examples of the invention are intended to illustrate, but not to limit, the present invention.

EXAMPLES

Hereinbelow, the results of measurements for high molecular weight assay-objects: C-reactive protein (CRP; molecular weight: 120,000); a high density lipoprotein (HDL: molecular weight: about 400,000); a low density lipoprotein (LDL; molecular weight 3,000,000); and enterohemorrhagic *E. coli* O157 (*E. coli* O157; size: 2 μm) according to the present invention will be described. An anti-CRP polyclonal antibody, an anti-HDL polyclonal antibody, an anti-LDL polyclonal antibody, and anti-*E. coli* O157 polyclonal antibody, each labeled with a pyrene derivative, were used in the measurements. The pyrene derivative is a fluorochrome having a fluorescence lifetime of about 50 nanoseconds to about 500 nanoseconds which correspond to a change in molecular weight from about 100,000 to about 5,000,000. F-4000 manufactured by Hitachi Ltd. was used as an apparatus for measuring the degree of fluorescence polarization.

Example 1
Synthesis of Succinimidyl-1-pyrenebutanoic Acid (SPB)

Figure 2:
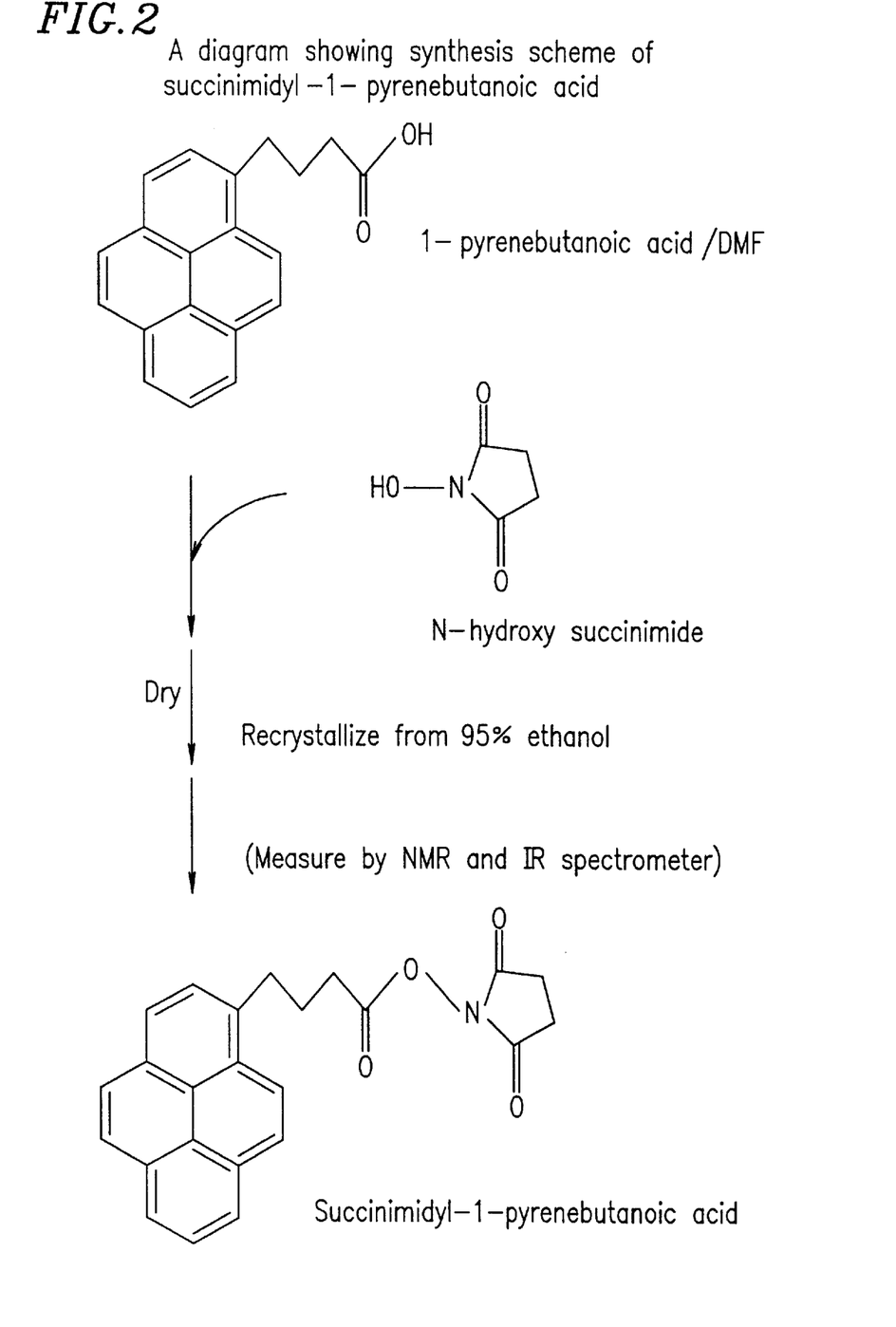
FIG. 2 is a diagram showing a synthesis scheme of a succinimidyl-1-pyrenebutanoic acid.

SPB was prepared according to the synthesis scheme shown in FIG. 2. In 20 ml of dimethylsulfoxide (DMF), 2.25 g of 1-pyrenebutanoic acid (7.8 mmol: obtained from Molecular Probes, Inc.) and 1.2 g of N-hydroxy succinimide (10.4 mmol: obtained from Wako Pure Chemical Industries, Ltd.) were dissolved. After the mixed solution was cooled to 0° C., 2.69 g of 1,3-dichlorohexylcarbodiimide (13.1 mmol: DCC) was added thereto. Then, the mixture was reacted at 0° C. for 24 hours while stirring. After the reacted solution was filtered with a 0.45 μm filter, the filtrate was collected and dried using an evaporator. Then, the filtrate was recrystallized from 95% ethanol, thereby obtaining 1.88 g of succinimidyl-1-pyrenebutanoic acid (yield: 70%).

The obtained SPB was analyzed by an IR spectrometer and NMR. The infrared absorption of the carboxyl group (1692 $cm^{-1}$) disappeared, and the infrared absorption of the imide group (1783 $cm^{-1}$, 1785 $cm^{-1}$ and 1817 $cm^{-1}$) appeared. Also from the results of NMR for $^1H$ and $^{13}C$, the product was identified as SPB.

Example 2
Preparation of Pyrene-labeled Polyclonal Antibody

A pyrene-labeled polyclonal antibody was prepared as described below, using an anti-CRP polyclonal antibody (obtained from Bio Reactive), an anti-HDL polyclonal antibody (obtained from Cosmo Bio Co., Ltd.), an anti-LDL polyclonal antibody (obtained from Cosmo Bio Co., Ltd.), and an anti-*E. coli* O157 polyclonal antibody (obtained from Funakoshi) together with SPB synthesized in Example 1 above.

A respective solution (1000 μl) containing 2.0 mg/ml of each of the polyclonal antibodies in a phosphate-buffered saline (PBS), pH 7.4, was mixed with a solution (20 μl) containing 1.29 mg/ml of SPB (5-fold amount of antibody) dissolved in dimethylsulfoxide (DMSO). These mixed solutions were reacted at room temperature for 4 hours while stirring. The reacted solutions were each subjected to SEPHADEX® G-25 gel filtration column (Pharmacia) (size: 10×60 mm, flow rate: about 2 ml/min). Unreacted SPB was removed, and fractions containing the pyrene-labeled polyclonal antibody were collected.

The collected fractions were used to evaluate the labeling amount and the fluorescence property of the prepared pyrene-labeled polyclonal antibody.

Figure 3:
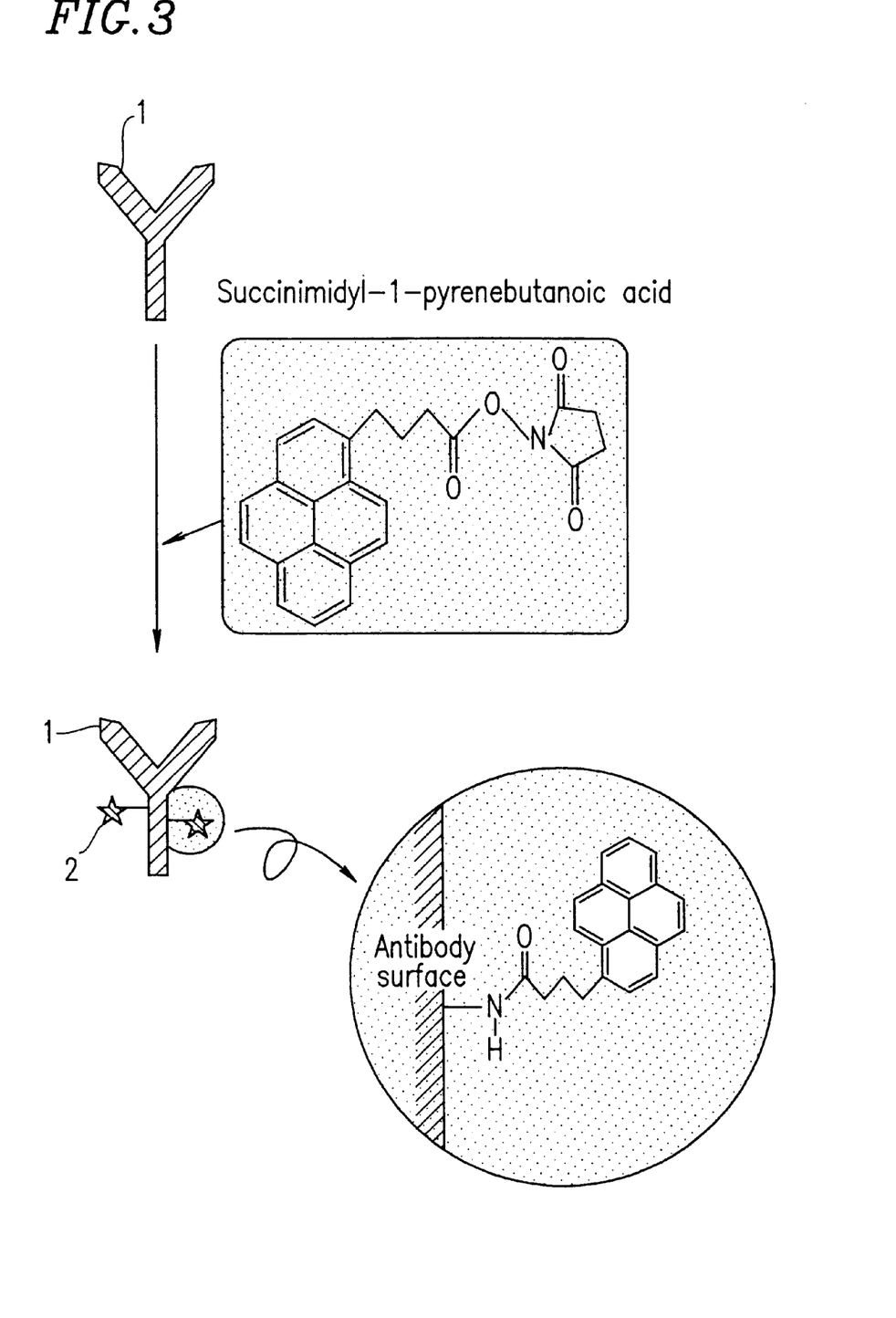
FIG. 3 is a concept diagram showing the labeling of an antibody with fluorochromes.

The labeling amount was measured using an ultraviolet/visible spectrometer (manufactured by Shimadzu Corp., UV-1600PC), confirming labeling of: 1.1 pyrenes per one molecule of the anti-CRP polyclonal antibody; 0.9 pyrene per one molecule of the anti-HDL polyclonal antibody; 0.5 pyrene per one molecule of the anti-LDL polyclonal antibody; and 1.2 pyrenes per one molecule of the anti-*E. coli* O157 polyclonal antibody. FIG. 3 shows an image of pyrene binding to an antibody.

The fluorescence property was measured using a fluorescence spectrometer (manufactured by Shimadzu Corp., RF-5300PC), finding that the fluorescence property of pyrene bound to each of the labeled antibodies was such that the excitation wavelength was 330 nm and the resulting fluorescence wavelengths were 373 nm and 397 nm. Since the fluorescence intensity was greater at 397 nm, as the measurement conditions to be used with the fluorescence polarization method, it was determined to utilize the excitation wavelength of 330 nm and the fluorescence wavelength of 397 nm.

Example 3

Measurement of CRP with Pyrene-labeled Anti-CRP Polyclonal Antibody

A solution (700 µl) containing the pyrene-labeled anti-CRP polyclonal antibody at 400 µg/ml was placed into a cuvette (5×5 mm) so as to measure the degree of fluorescence polarization. The measurement conditions for the pyrene-labeled anti-CRP polyclonal antibody were as follows: a measurement temperature of 35° C., an excitation wavelength of 330 nm, a fluorescence wavelength of 397 nm and a G factor of 0.942.

Figure 4:
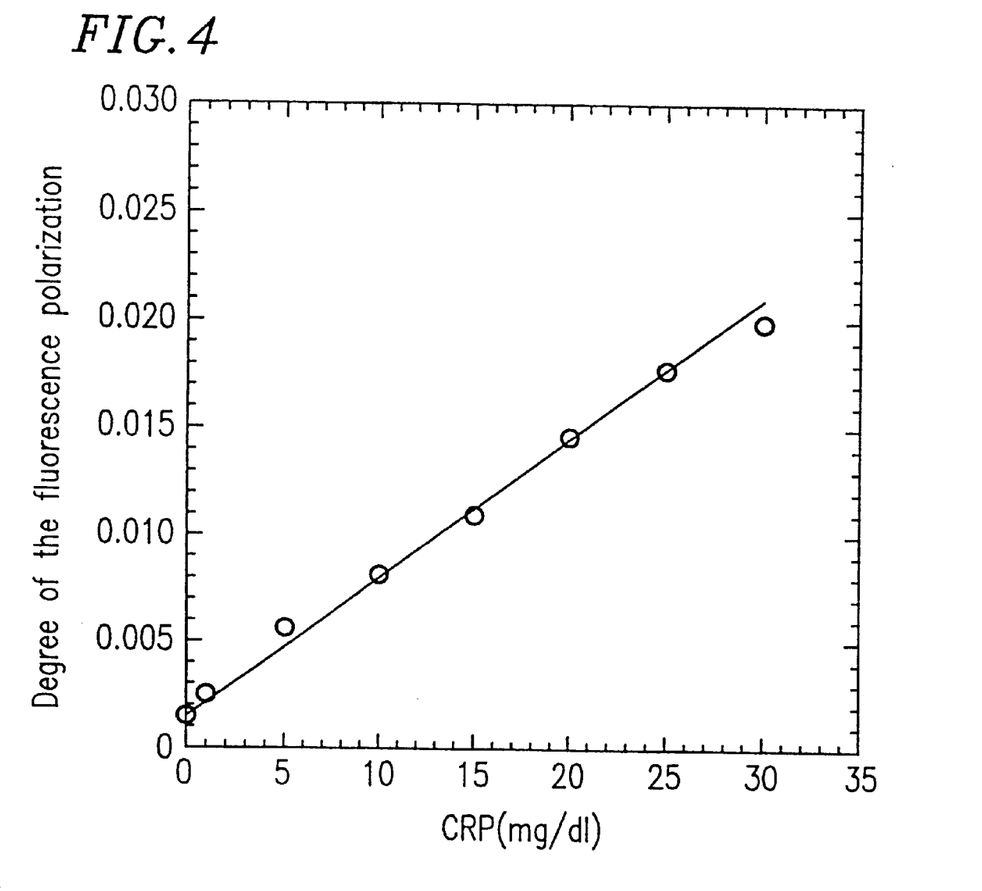
FIG. 4 is a graph showing measurement results of the fluorescence polarization method of the present invention for C-reactive protein (CRP).

A CRP solution having a CRP concentration of 0 to 50 mg/dl (obtained from O.E.M. Concepts, Inc.) was prepared. The above-described antibody solution (700 µl) and the CRP solution (30 µl) were mixed with each other, and stirred at 35° C. for 0.5 minute, after which the degree of fluorescence polarization was measured under the above-described conditions for 0.5 minute, thereby measuring the change in the degree of fluorescence polarization. As a result, it was found that up to a 30 mg/dl concentration could be measured for CRP. The results are shown in FIG. 4.

Example 4

Measurement of HDL with Pyrene-labeled Anti-HDL Polyclonal Antibody

A solution (700 µl) containing the pyrene-labeled anti-HDL polyclonal antibody at 400 µg/ml was placed into a cuvette (5×5 mm) so as to measure the degree of fluorescencepolarization. The measurement conditions for the pyrene-labeled anti-HDL polyclonal antibody were as follows: a measurement temperature of 35° C., an excitation wavelength of 330 nm, a fluorescence wavelength of 397 nm and a G factor of 0.943.

Figure 5:
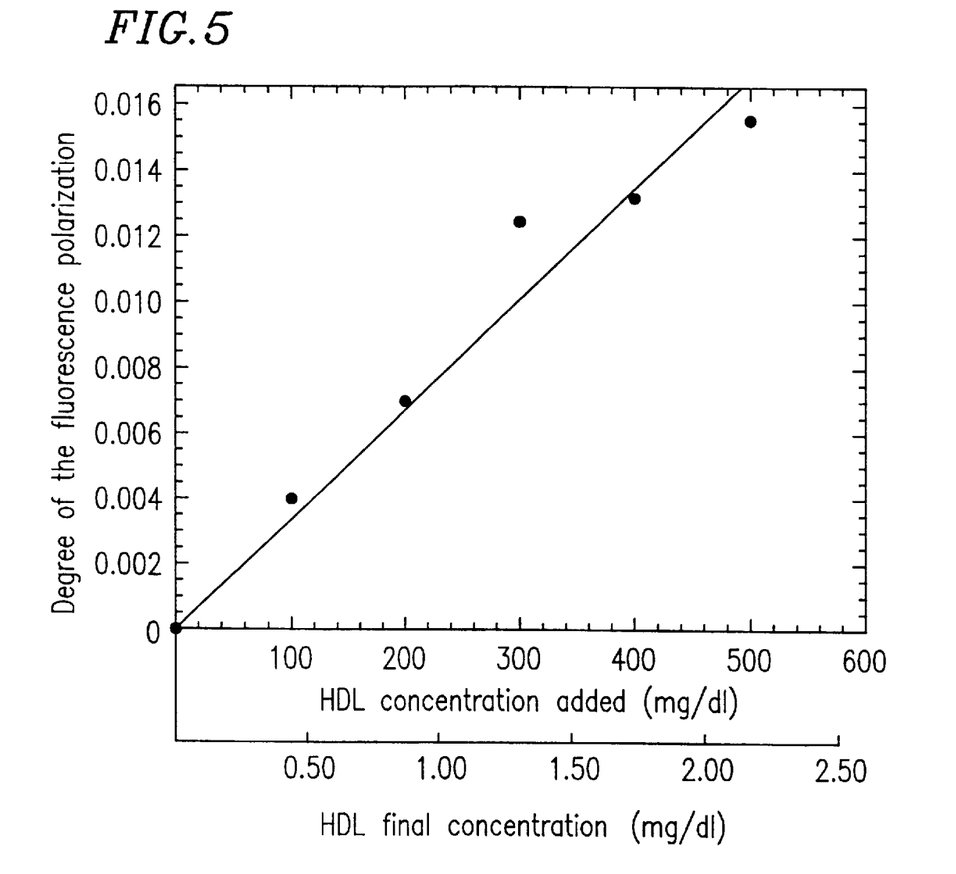
FIG. 5 is a graph showing measurement results of the fluorescence polarization method of the present invention for a high density lipoprotein (HDL).

An HDL solution having an HDL concentration of 0 to 500 mg/dl (obtained from Cosmo Bio Co., Ltd.) was prepared. The above-described antibody solution (700 µl) and the HDL solution (5 µl) were mixed with each other, and stirred at 35° C. for 0.5 minute, after which the degree of fluorescence polarization was measured under the above-described conditions for 0.5 minute, thereby measuring the change in the degree of fluorescence polarization. As a result, it was found that up to a 500 mg/dl concentration could be measured for HDL. The results are shown in FIG. 5.

Example 5

Measurement of LDL with Pyrene-labeled Anti-LDL Polyclonal Antibody

A solution (700 µl) containing the pyrene-labeled anti-LDL polyclonal antibody at 400 µg/ml was placed into a cuvette (5×5 mm) so as to measure the degree of fluorescence polarization. The measurement conditions for the pyrene-labeled anti-LDL polyclonal antibody were as follows: a measurement temperature of 35° C., an excitation wavelength of 330 nm, a fluorescence wavelength of 397 nm and a G factor of 0.943.

Figure 6:
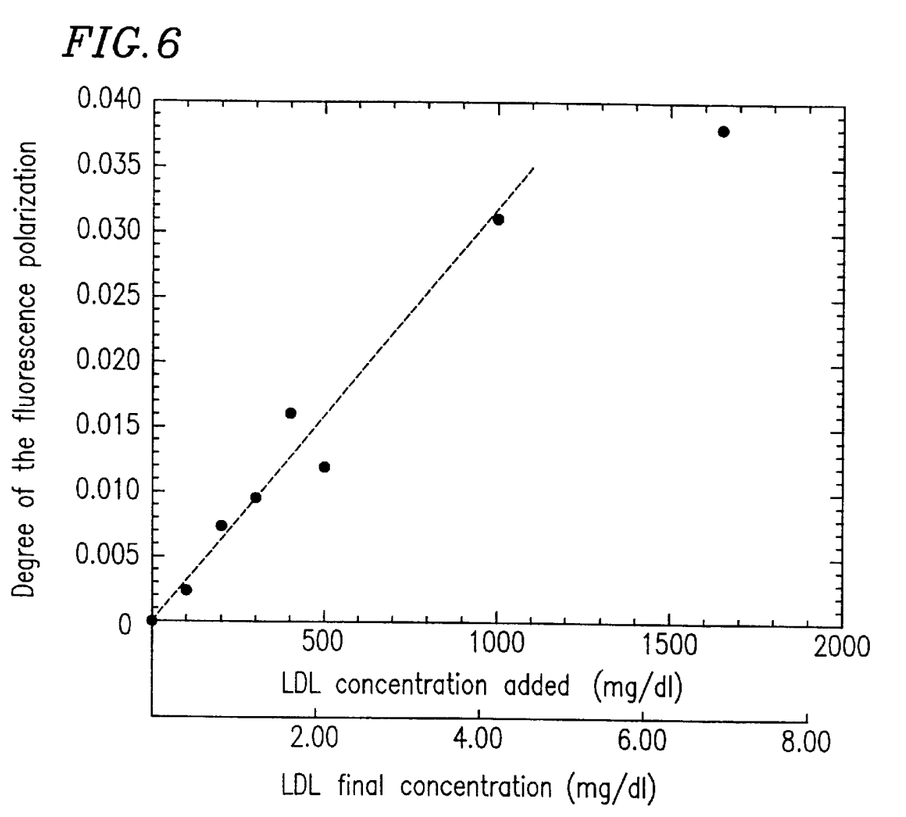
FIG. 6 is a graph showing measurement results of the fluorescence polarization method of the present invention for a low density lipoprotein (LDL).

An LDL solution having an LDL concentration of 0 to 1650 mg/dl (obtained from Cosmo Bio Co., Ltd.) was prepared. The above-described antibody solution (700 µl) and the LDL solution (5 µl) were mixed with each other, and stirred at 35° C. for 0.5 minute, after which the degree of fluorescence polarization was measured under the above-described conditions for 0.5 minute, thereby measuring the change in the degree of fluorescence polarization. As a result, it was found that up to a 1000 mg/dl concentration could be measured for LDL. The results are shown in FIG. 6.

Example 6

Measurement of LDL with Pyrene-labeled Anti-*E.coli* O157 Polyclonal Antibody

A solution (700 µl) containing the pyrene-labeled anti-*E.coli* O157 polyclonal antibody at 400 µg/ml was placed into a cuvette (5×5 mm) so as to measure the degree of fluorescence polarization. The measurement conditions for the pyrene-labeled anti-*E.coli* O157 polyclonal antibody were as follows: a measurement temperature of 35° C., an excitation wavelength of 330 nm, a fluorescence wavelength of 397 nm and a G factor of 0.942.

Figure 7:
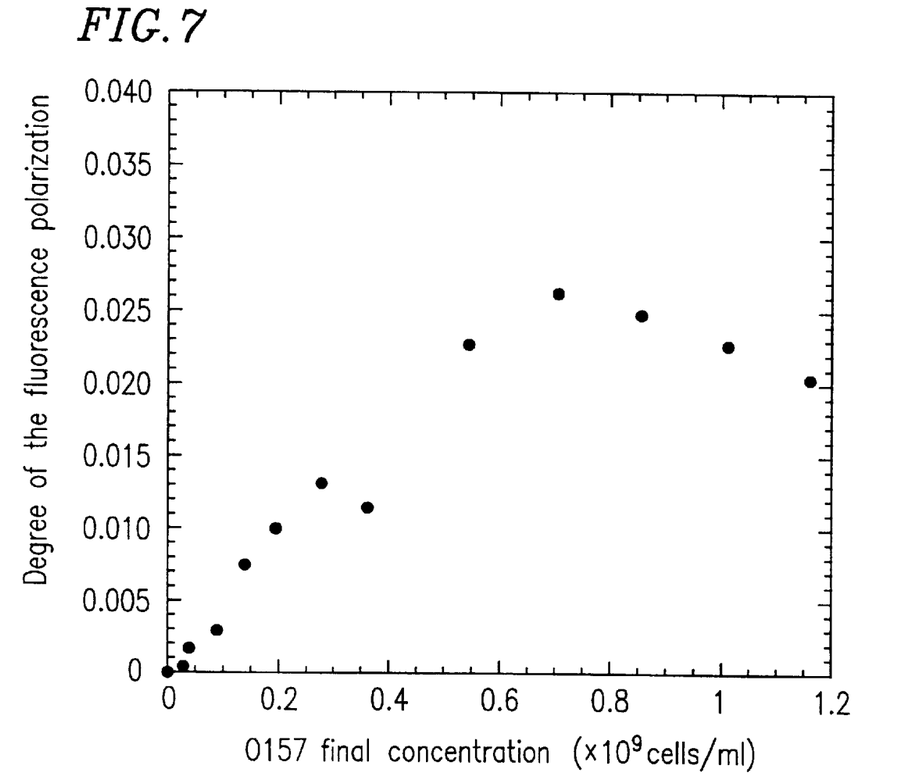
FIG. 7 is a graph showing measurement results of the fluorescence polarization method of the present invention for *E. coli* O157.

An *E.coli* O157 (obtained from Funakoshi) solution was added to the above-described antibody solution (700 µl) so that the final concentration is 0 to $1.2 \times 10^9$ cells/ml. The mixed solution was stirred at 35° C. for 0.5 minute, after which the degree of fluorescence polarization was measured under the above-described conditions for 0.5 minute, thereby measuring the change in the degree of fluorescence polarization. As a result, it was found that up to a $1.0 \times 10^8$ cells/ml concentration could be measured for *E.coli* O157. The results are shown in FIG. 7.

INDUSTRIAL APPLICABILITY

The method of the present invention provides a fluorescence polarization method with a simple assay reaction system and an easy assay operation, and particularly a method which is suitable for an assay of a high-molecular-weight substance.

What is claimed is:

1. A fluorescence polarization method for analyzing an assay-object in a sample, the method comprising the steps of:
    (a) providing a fluorescent-labeled protein in which a protein is covalently bound to a fluorochrome, wherein the protein is an antibody, a receptor or an inhibitor, which is capable of specifically binding to the assay-object;
    (b) allowing the fluorescent-labeled protein to bind to the assay-object; and
    (c) measuring a change in the degree of fluorescence polarization which has taken place in the fluorescent-labeled protein by its binding to the assay-object,
    wherein said fluorochrome has a skeletal structure of pyrene, and said protein is bound by a peptide bond to said fluorochrome.

2. A fluorescence polarization method according to claim 1, wherein the antibody is a polyclonal antibody, a monoclonal antibody, a chimeric antibody, a Fab antibody or a (Fab)2 antibody.

3. A fluorescence polarization method according to claim 1, wherein the assay-object is a biological substance, a microorganism, a virus, a pharmaceutical, an environmental pollutant or an abused drug.

4. A fluorescence polarization method according to claim 3, wherein the biological substance is a peptide, a protein, a lipid, a saccharide or a nucleic acid.

5. A fluorescence polarization method according to claim 4, wherein the protein has a molecular weight of 500,000 or more.

6. A fluorescence polarization method according to claim 4, wherein the protein is an antibody, a hormone, an inflammation marker, a coagulation factor, an apolipoprotein, a high density lipoprotein (HDL), a low density lipoprotein (LDL), a glycosylated albumin, a glycosylated hemoglobin, a hemoglobin, a cancer marker or an enzyme.

7. A fluorescence polarization method according to claim 6, wherein the hormone is chorionic gonadotropin, thyroid-stimulating hormone, progesterone, follicular forming hormone, parathyroid-stimulating hormone, adrenocorticotropic hormone, or insulin.

8. A fluorescence polarization method according to claim 6, wherein the inflammation marker is C-reactive protein (CRP), α1-antitrypsin (α1-AT), (α1-antichymotrypsin (α1-X), α1-acid glycoprotein (α1-AG), haptoglobin (Hp), ceruloplasmin (Cp), the 9th component of complement (C9), the 4th component of complement (C4), the 3rd component of complement (C3), complement factor B (B), fibrinogen (Fbg), serum amyloid A (SAA), C1 inhibitor (C1I), a sialoglycoprotein, an acid-soluble protein (ASP) or an immunosuppressive acidic protein (IAP).

9. A fluorescence polarization method according to claim 1, wherein a lifetime of fluorescence of the fluorochrome is in the range of 10 nanoseconds to 200 nanoseconds.

10. A reagent for use in the fluorescence polarization method of claim 1, the reagent comprising a fluorescent-labeled protein in which a protein is covalently bound to a fluorochrome(s), wherein the protein is an antibody, a receptor or an inhibitor, which is capable of specifically binding to the assay-object,
wherein said fluorochrome has a skeletal structure of pyrene, and said protein is bound by a peptide bond to said fluorochrome.

11. A fluorescence polarization method for analyzing a bacteria or a virus in a sample, the method comprising the steps of:
(a) providing a fluorescent-labeled antibody in which an antibody is covalently bound to a fluorochrome, wherein the antibody is capable of specifically binding to the bacteria or the virus;
(b) allowing the fluorescent-labeled antibody to bind to the bacteria or the virus; and
(c) measuring a change in the degree of fluorescence polarization which has taken place in the fluorescent-labeled antibody by its binding to the bacteria or the virus,
wherein said fluorochrome has a skeletal structure of pyrene, and said protein is bound by a peptide bond to said fluorochrome.

12. A fluorescence polarization method according to claim 11, wherein the antibody is a polyclonal antibody, a monoclonal antibody, a chimeric antibody, a Fab antibody or a (Fab)2 antibody.

13. A fluorescence polarization method according to claim 11, wherein the bacteria is selected from the group consisting of Rhodospirillaceae, Chromatiaceae, Chlorobiaceae, Myxococcaceae, Archangiaceae, Cystobacteraceae, Polyangiaceae, Cytophagaceae, Beggiatoaceae, Simonsiellaceae, Leucotrichaceae, Achromatiaceae,; Pelonemataceae, Spirochaetaceae, Spirillaceae, Pseudomonadaceae, Azotobacteraceae, Rhizobiceae, Methylomonadaceae, Halobacteriaceae, Enterobacteriaceae, Vibrionaceae, Bacteroidaceae, Neisseriaceae, Veillonellaceae, bacterial organisms oxidizing ammonia or nitrite, bacterial organisms metabolizing sulfur and sulfur compounds, bacterial organisms depositing iron or manganese oxides, Siderocapsaceae, Methanobacteriaceae, Aerobic and facultatively anaerobic Micrococcaceae, Streptococcaceae, Anaerobic Peptococcaceae, Bacillaceae, Lactobacillaceae, Coryneform group of bacteria, Propionibacteriaceae, Actinomycetaceae, Mycobacteriaceae, Frankiaceae, Actinoplanaceae, Dermatophilaceae, Nocardiaceae, Streptomycetaceae, Micromonosporaceae, Rickettsiaceae, Bartonellaceae, Anaplasmataceae, Chlamydiaceae, Mycoplasmataceae and Acholeplasmataceae.

14. A fluorescence polarization method according to claim 11, wherein the virus is selected from the group consisting of Enterovirus, Cardiovirus, Rhinovirus, Aphthovirus, Calicivirus, Orbivirus, Reovirus, Rotavirus, Abibirnavirus, Piscibirnavirus, Entomobirnavirus, Alphavirus, Rubivirus, Pestivirus, Flavivirus, Influenzavirus, Pneumovirus, Paramyxovirus, Morbillivirus, Vesiculovirus, Lyssavirus, Coronavirus, Bunyavirus, Arenavirus, Human immunodeficiency virus, Hepatitis A virus, Hepatitis B virus and Hepatitis C virus.

15. A fluorescence polarization method according to claim 11, wherein a lifetime of fluorescence of the fluorochrome is in the range of 10 nanoseconds to 200 nanoseconds.

16. A reagent according to claim 10, wherein the assay-object is a bacteria or a virus, and the specifically-binding protein is an antibody.

17. A fluorescence polarization method according to claim 1, wherein the fluorochrome has a skeletal structure of pyrene that is bound to the protein by a peptide bond by reaction between (i) a functional group on pyrene and (ii) a group on the protein selected from the group consisting of a primary amino group, a secondary amino group, a tertiary amino group, and a carboxyl group.

18. A fluorescence polarization method according to claim 11, wherein the fluorochrome has a skeletal structure of pyrene that is bound to the protein by a peptide bond by reaction between (i) a functional group on pyrene and (ii) a group on the protein selected from the group consisting of a primary amino group, a secondary amino group, a tertiary amino group, and a carboxyl group.

* * * * *

UNITED STATES PATENT AND TRADEMARK OFFICE
CERTIFICATE OF CORRECTION

PATENT NO. : 6,432,632 B2  Page 1 of 1
DATED : August 13, 2002
INVENTOR(S) : Hiroshi Nakayama and Jinsei Miyazaki It is certified that error appears in the above-identified patent and that said Letters Patent is hereby corrected as shown below:

Column 11,
Line 24, "(α1-antichymotrypsin (α1-X)" should be -- α1-antichymotrypsin (α1 - X) --.

Column 12,
Line 12, "Rhizobiceae" should be -- Rhizobiaceae --.

Signed and Sealed this

Tenth Day of December, 2002

JAMES E. ROGAN
*Director of the United States Patent and Trademark Office*